United States Patent [19]

Maule

[11] Patent Number: 5,415,842
[45] Date of Patent: May 16, 1995

[54] SURFACE PLASMON RESONANCE ANALYTICAL DEVICE

[75] Inventor: Colin H. Maule, Cambridge, United Kingdom

[73] Assignee: Fisons plc, Ipswich, Great Britain

[21] Appl. No.: 94,032

[22] PCT Filed: Feb. 3, 1992

[86] PCT No.: PCT/GB92/00192
§ 371 Date: Jul. 19, 1993
§ 102(e) Date: Jul. 19, 1993

[87] PCT Pub. No.: WO92/14140
PCT Pub. Date: Aug. 20, 1992

[30] Foreign Application Priority Data

Feb. 7, 1991 [GB] United Kingdom ............. 9102646

[51] Int. Cl.⁶ ............................................. G01N 21/17
[52] U.S. Cl. ................................. 422/82.05; 356/445
[58] Field of Search .............. 422/82.05, 82.08–82.11; 356/445

[56] References Cited

U.S. PATENT DOCUMENTS 5,229,833  7/1993  Stewart ........................... 356/364

FOREIGN PATENT DOCUMENTS 0286195  4/1988  European Pat. Off. .
0305109  8/1988  European Pat. Off. .
0346016  6/1989  European Pat. Off. .
0353937  7/1989  European Pat. Off. .

OTHER PUBLICATIONS

Liedberg et al., "Surface Plasmon Resonance for Gas Detection and Biosensing", Sensors and Actuators, 4(1983), pp. 299–304.

Quail et al., "Long Range Surface-Plasmon Modes in Silver and Aluminum Films", Optics Letters vol. 8, No. 7, Jul. 1983, pp. 377–379.

*Primary Examiner*—Lyle A. Alexander
*Attorney, Agent, or Firm*—Marshall, O'Toole, Gerstein, Murray & Borun

[57] ABSTRACT

A long-range SPR sensor includes: (a) a source of electromagnetic radiation, (b) an optical structure including a block of material transparent to the electromagnetic radiation, a spacer layer of dielectric material, a metallic layer, and a sensitive layer capable of reaction with a sample to be tested, and (c) apparatus for monitoring radiation from the source which is incident upon the block and which is internally reflected at the interface between the block and the spacer layer. A thin layer of dielectric material of high refractive index is interposed between the metallic layer and the layer of sensitive material. The provision of the thin layer of dielectric material between the metal layer and the sample under test enables the advantages of long-range SPR to be more fully realized, notably a very sharp resonance with corresponding improvements in sensitivity.

9 Claims, 1 Drawing Sheet

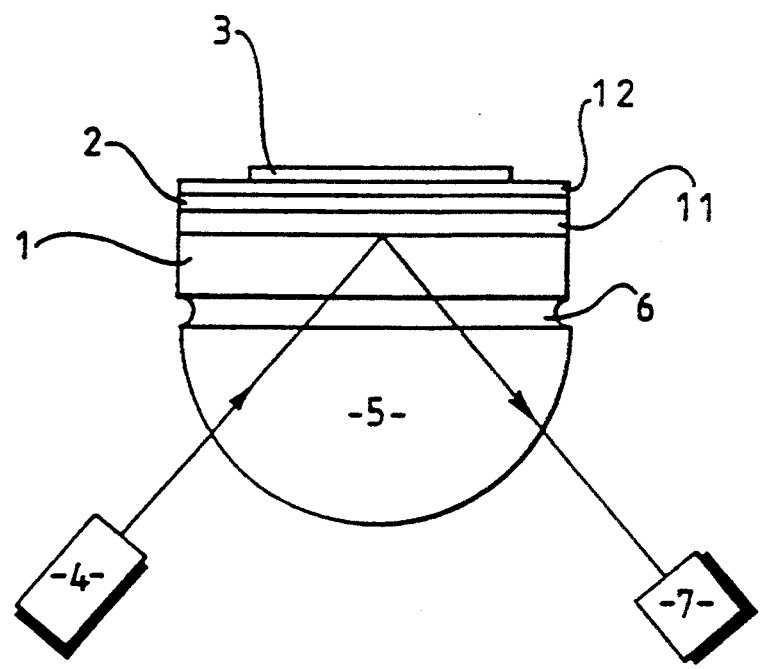

SURFACE PLASMON RESONANCE ANALYTICAL DEVICE

FIELD OF THE INVENTION

This invention relates to sensors for the detection of chemical species, in particular to sensors for the detection of analytes in solution by the technique of long range surface plasmon resonance (SPR).

BACKGROUND OF THE INVENTION

SPR is well known for the detection of chemical species. SPR may be achieved by using the evanescent wave which is generated when a polarized light beam is totally internally reflected at the interface between a dielectric medium, eg glass, and a thin layer of metal. The technique is described by Lieberg et al in Sensors and Actuators, 4, 299. The basis for the application of SPR to sensing is the fact that the .oscillation of the surface plasma of free electrons which exists at a metal-dielectric boundary is affected by the refractive index of the material adjacent to the metal surface. Resonance occurs when the angle of incidence of the radiation has a particular value, and this value is dependent on the refractive index of the material adjacent to the metal. Thus, changes in this refractive index give rise to changes in the angle at which resonance occurs. Resonance may be detected as a dip in the intensity of the internally reflected beam.

In a typical SPR device, the thin layer of metal is coated on the surface of a glass prism. Recently, European Patent Application number 0346016 (Amersham) has suggested that the sensitivity of an SPR device may be enhanced by using the phenomenon of long range SPR. Long range SPR is described by Quail et al in Optics Letters, 8, 377 and involves a thin metal layer isolated from a coupling prism by a low refractive index "spacer" layer. This extra layer allows excitation of an SPR resonance on both metal dielectric interfaces, top and bottom, as opposed to the single resonance seen when just a metal layer is used. If the metal layer is thin enough, the field profiles from the two resonances will overlap, and they will have the opportunity to interact, provided that certain conditions are met. In particular, the propagation constants k of the two resonances must match, or at least be close to matching. Interaction will produce an anti-symmetric and a symmetric combination of the fields, labelled long range and short range SPR respectively. The anti-symmetric combination has a greater proportion of its field outside of the metal layer, and so suffers less loss, travels further along the surface (hence the name), and has a narrower resonance. The symmetric combination travels a shorter distance along the surface, and has a broader resonance.

The condition for matching propagation constants has conventionally required the presence of dielectrics of the same refractive index at the two interfaces. This is a problem in sensors, eg biosensors, in which the sample under test is aqueous (blood plasma, for instance) and has a refractive index of approximately 1.33. Spacer materials having refractive indices close to this value are not common, and those which are available cannot readily be coated with a thin layer of metal. Magnesium fluoride has a refractive index of about 1.38, which is close enough to show coupling, but is some way from optimal.

We have now devised a long range SPR device in which the above mentioned problem is overcome or substantially mitigated.

SUMMARY OF THE INVENTION

According to the invention, there is provided a long range SPR sensor comprising:
  (a) a source of electromagnetic radiation,
  (b) an optical structure comprising a block of material transparent to said electromagnetic radiation, a spacer layer of dielectric material, a metallic layer and a sensitive layer capable of reaction with a sample to be tested, and
  (c) means for monitoring radiation from the source which is incident upon the block and which is internally reflected at the interface between the block and the spacer layer,
characterised in that a thin layer of dielectric material of high refractive index is interposed between the metallic layer and the layer of sensitive material.

The sensor according to the invention is advantageous in that the presence of the high refractive index dielectric between the metal layer and the sample under test results in a closer matching of the SPR propagation constants at the two metal surfaces. This enables the advantages of long range SPR to be more fully realised, notably a very sharp resonance with corresponding improvements in sensitivity. Further, these advantages may be realised while using readily available and otherwise suitable materials for the spacer layer, eg silica.

The refractive index of the high refractive index dielectric layer should be sufficiently high to raise the effective index of the combination of sample and high refractive index layer to that of the spacer layer. The effective refractive index may also be increased by increasing the thickness of the extra layer and, in general, for best results it is necessary to optimise the thicknesses of all three layers. However, the high refractive index dielectric layer must be thin enough for the evanescent field to penetrate substantially into the sample, in order to provide sensitivity to changes occurring in the sensitive layer.

The nature of the transparent block, the source of electromagnetic radiation and the detector will be apparent to those familiar with conventional SPR devices. By way of example, attention may be drawn to European Patent Application No 0305109 (Amersham) which describes such a device as well as to European Patent Application No 0346016 referred to above. In summary:
  the block is conveniently of glass, eg in the form of a glass chip or prism,
  the metallic coating is most conveniently of silver,
  the light source is any source which has a small spectral width and good coherence, eg a laser,
  the means for monitoring reflected radiation may be any of those conventionally employed, eg photo multipliers and charge-coupled devices.

The sensitive layer will generally be sensitised by the inclusion of specific binding partners for the analyte under test, suitable such binding partners and methods for their immobilisation upon the high refractive index dielectric layer being apparent to those skilled in the art.

The resonant condition may be detected by varying the angle of incidence of the radiation from the source, either by varying the angle of incidence sequentially or by simultaneously irradiating at a range of wavelengths.

BRIEF DESCRIPTION OF THE DRAWING

An embodiment of the present invention will now be described by way of illustration only, with reference to the accompanying drawing in which:

FIG. 1 is a schematic view of a sensor according to the invention.

DESCRIPTION OF PREFERRED EMBODIMENTS

A biosensor for the determination of an antigen in a sample of body fluid comprises a glass slide (1) coated on one surface with a layer of silica (11) which in turn is coated with a thin layer of silver (2). The layer of silver (2) is coated with a thin layer of zirconia (12) upon which is immobilised a layer (3) of antibodies to the antigen under test. Light from a laser light source (4) is coupled into the slide (1) by a hemi-cylindrical prism (5) and a layer of index matching fluid (6).

Total internal reflection occurs at the glass-silica interface and the reflected beam is coupled out of the slide (1) by the matching fluid (6) and prism (5). The intensity of the reflected light beam is measured by a detector (7).

The silica layer (11) has a thickness of approximately 2000 nm, the silver layer (2) a thickness of approximately 23 nm and the zirconia layer (12) a thickness of approximately 18 nm.

The angle of incidence of light from the light source (4) at which long range surface plasmon resonance occurs is detected by varying the angle of incidence. At resonance a sharp dip is observed in the intensity of light internally reflected at the interface between the glass slide (1) and the silica layer (11). When a sample containing the analyte under test is brought into contact with the layer of immobilised antibodies (3) a specific binding reaction occurs which changes the refractive index in the vicinity of the surface of the device. The results in a shift in the angular position of resonance which may be qualitatively and/or quantitatively related to the presence of analyte in the sample.

I claim:

1. A long range surface plasmon resonance sensor comprising:
   (a) a source of electromagnetic radiation (4),
   (b) an optical structure comprising a block (1) of material transparent to said electromagnetic radiation, a spacer layer (11) of dielectric material, a metallic layer (2) and a sensitive layer (3) capable of reaction with a sample to be tested, and
   (c) means (7) for monitoring radiation from the source (4) which is incident upon the block (1) and which is internally reflected at the interface between the block (1) and the spacer layer (11), further comprising a thin layer of dielectric material (12) of high refractive index interposed between the metallic layer (2) and the layer of sensitive material (3).

2. A sensor as claimed in claim 1, wherein the thin layer of dielectric material (12) is of zirconia.

3. A sensor as claimed in claim 1, wherein the spacer layer (2) is of silica.

4. A sensor as claimed in claim 1, wherein the block (1) is of glass.

5. A sensor as claimed in claim 1, wherein the metallic coating (2) is of silver.

6. A sensor as claimed in claim 1, wherein the light source (4) is a laser.

7. A sensor as claimed in claim 1, wherein the means (7) for monitoring reflected radiation is a photo multiplier or a charge-coupled device.

8. A sensor as claimed in claim 1, wherein the sensitive layer (3) is sensitised by the inclusion of specific binding partners for the analyte under test.

9. A sensor as claimed in claim 1, wherein the resonant condition is detected by varying the angle of incidence of the radiation from the source (4), either by varying the angle of incidence sequentially or by simultaneously irradiating at a range of wavelengths.

* * * * *